(12) United States Patent
Kim et al.

(10) Patent No.: US 10,646,423 B2
(45) Date of Patent: May 12, 2020

(54) COSMETIC PRODUCT HAVING EXCELLENT UV-BLOCKING EFFECT AND MANUFACTURING METHOD THEREOF

(71) Applicant: CQV CO., LTD., Jincheon-gun, Chungcheongbuk-do (KR)

(72) Inventors: Ki-Jung Kim, Cheongju-si (KR); Sang-Hoon Kim, Cheongju-si (KR); Kwang-Choong Kang, Cheongju-si (KR); Byung-Ki Choi, Cheongju-si (KR); Kwang-Soo Lim, Jincheon-gun (KR); Kil-Wan Chang, Cheongju-si (KR)

(73) Assignee: CQV CO., LTD., Jincheon-Gun, Chungcheongbuk-Do (KR)

( * ) Notice: Subject to any disclaimer, the term of this patent is extended or adjusted under 35 U.S.C. 154(b) by 0 days.

(21) Appl. No.: 15/538,888

(22) PCT Filed: Dec. 22, 2016

(86) PCT No.: PCT/KR2016/015134
§ 371 (c)(1),
(2) Date: Jun. 22, 2017

(87) PCT Pub. No.: WO2017/135569
PCT Pub. Date: Aug. 10, 2017

(65) Prior Publication Data
US 2018/0049959 A1    Feb. 22, 2018

(30) Foreign Application Priority Data

Feb. 2, 2016    (KR) .................. 10-2016-0013078

(51) Int. Cl.
| A61K 8/25 | (2006.01) |
| A61K 8/02 | (2006.01) |
| A61Q 17/04 | (2006.01) |
| A61K 8/29 | (2006.01) |

(52) U.S. Cl.
CPC .................. *A61K 8/29* (2013.01); *A61K 8/02* (2013.01); *A61K 8/0279* (2013.01); *A61K 8/25* (2013.01); *A61Q 17/04* (2013.01); *A61K 2800/436* (2013.01); *A61K 2800/621* (2013.01)

(58) Field of Classification Search
None
See application file for complete search history.

(56) References Cited

U.S. PATENT DOCUMENTS

| 4,192,691 | A | 3/1980 | Armani | |
| 5,611,851 | A | 3/1997 | Deluca et al. | |
| 2009/0186055 | A1* | 7/2009 | Dumousseaux | ......... A61K 8/11 424/401 |
| 2011/0104220 | A1* | 5/2011 | Schmidt | .............. A61K 8/0275 424/401 |
| 2015/0290090 | A1* | 10/2015 | Matsufuji | ................. A61K 8/29 424/401 |

FOREIGN PATENT DOCUMENTS

| CN | 102906024 A | 1/2013 |
| JP | 2001-199838 A | 7/2001 |
| JP | 2002-265331 A | 9/2002 |
| JP | 2003-171575 A | 6/2003 |
| JP | 2007-277107 A | 10/2007 |
| JP | 2013-501078 A | 1/2013 |
| JP | 2013-527209 A | 6/2013 |
| JP | 2013-139403 A | 7/2013 |
| JP | 2014-205644 A | 10/2014 |
| JP | 2015-522066 A | 8/2015 |
| KR | 2003-0046440 A | 6/2003 |
| KR | 1020090069328 A | 6/2009 |
| KR | 10-2011-0058218 A | 6/2011 |
| KR | 10-2012-0050951 A | 5/2012 |
| KR | 10-2014-0070035 A | 6/2014 |
| KR | 10-1538271 B1 | 7/2015 |
| WO | 2011-151184 A1 | 12/2011 |
| WO | 2011151184 A1 | 12/2011 |
| WO | 2014-010101 A1 | 1/2014 |
| WO | 2014010101 A1 | 1/2014 |
| WO | 2014/098163 A1 | 6/2014 |

OTHER PUBLICATIONS

Machine translation for JP2002265331A; newly filed IDS reference. Published Sep. 18, 2002.*
International Search Report for PCT/KR2016/015134 dated Apr. 26, 2017.
Lee, Kwan-Sik et al., "Preparation and Chrominance of Metal Oxide Coated Titania/Mica Pearlescent Pigment", J. of Korea Oil Chemists' Soc., Jun. 2013, pp. 233-243, vol. 30, No. 2, Cheongju, Korea.
Korean Notice of Allowance dated Apr. 26, 2018, in connection with the Korean Patent Application No. 10-2016-0013078.
Extended European Search Report dated Jan. 3, 2018, corresponding to European Application No. 16874103.1.
Japanese Office Action dated Oct. 30, 2018, in connection with the Korean Patent Application No. 2017-561280.
European Search Report in connection with counterpart European Patent Application No. 16874103.1.
Chinese Office Action dated Dec. 18, 2019, in connection with the Chinese Patent Application No. 201680029999.X.

* cited by examiner

*Primary Examiner* — Jeffrey T. Palenik
(74) *Attorney, Agent, or Firm* — Hauptman Ham, LLP

(57) ABSTRACT

The present invention relates to a cosmetic product having an excellent UV-blocking effect and a manufacturing method thereof, in which the cosmetic product has an excellent UV-blocking effect, shows reduced whitening, has a good feeling in use, and good adhesion to the skin, and is not glossy and sticky after application to the skin, and to a manufacturing method thereof. The cosmetic product having an excellent UV-blocking effect according to the present invention includes: a cosmetic composition; and a hollow pearlescent pigment added to the cosmetic composition in an amount of 1 to 15 parts by weight based on 100 parts by weight of the cosmetic composition.

4 Claims, 2 Drawing Sheets

Example 1

Comparative Example 1

Comparative Example 2

COSMETIC PRODUCT HAVING EXCELLENT UV-BLOCKING EFFECT AND MANUFACTURING METHOD THEREOF

CROSS REFERENCE TO RELATED APPLICATION

This present application is a national stage filing under 35 U.S.C § 371 of PCT application number PCT/KR2016/015134 filed on Dec. 22, 2016 which is based upon and claims the benefit of priority to Korean Patent Application No. 10-2016-0013078 filed on Feb. 2, 2016 in the Korean Intellectual Property Office. The disclosures of the above-listed applications are hereby incorporated by reference herein in their entirety.

TECHNICAL FIELD

The present invention relates to a cosmetic product and a manufacturing method thereof, and more particularly to a cosmetic product having an excellent UV-blocking effect and a manufacturing method thereof, in which the cosmetic product has an excellent UV-blocking effect, shows reduced whitening, has a good feeling in use, and good adhesion to the skin, and is not glossy and sticky after application to the skin.

BACKGROUND ART

Cosmetics refer to products intended to be applied to or spread on the skin of the human body in order to cleanse or beautify the human body. Namely, cosmetics have been applied topically to the exposed portions of the skin in order to protect the skin from external factors such as sunlight, wind, rain and the like.

Such cosmetics can be divided into: skin care cosmetics intended to cleanse or beautify the human body to keep the skin healthy; makeup cosmetics such as loose powders, two-way cake foundations and the like, which are intended to enhance attraction; hair cosmetics such as hair lotions, hair creams and the like, which are intended to keep hair healthy and to beautify hair; and perfume.

As described above, skin care cosmetics or color makeup cosmetics are suitably used to keep the skin healthy and beautiful, so that the skin can be protected from dryness or UV rays, thereby keeping the skin bright and soft.

In recent years, products obtained by adding UV-blocking titanium dioxide to cosmetic compositions have been frequently used to protect the skin from UV rays.

However, the use of titanium dioxide as a UV-blocking agent has problems in that the titanium dioxide causes severe whitening, and gives a hard feeling due to its very small particle size to thereby reduce the feeling of the cosmetic product in use.

Prior art documents related to the present invention include Korean Patent Application Publication No. 10-2003-0046440 (published on Jun. 12, 2003) which discloses a cosmetic composition.

DISCLOSURE

Technical Problem

It is an object of the present invention to provide a cosmetic product having an excellent UV-blocking effect and a manufacturing method thereof, in which a lightweight hollow pearlescent pigment, from which a plate-like flake matrix was completely removed, is added to a cosmetic composition, so that the cosmetic product can exhibit an excellent UV-blocking effect and, at the same time, overcome the whitening problem.

Technical Solution

To achieve the above object, in one aspect, the present invention provides a cosmetic product having an excellent UV-blocking effect, the cosmetic product including: a cosmetic composition; and a hollow pearlescent pigment added to the cosmetic composition in an amount of 1 to 15 parts by weight based on 100 parts by weight of the cosmetic composition.

In another aspect, the present invention provides a method for manufacturing a cosmetic product having an excellent UV-blocking effect, the method including: (a) preparing a cosmetic composition; (b) preparing a hollow pearlescent pigment; and (c) mixing 1 to 15 parts by weight of the hollow pearlescent pigment with 100 parts by weight of the cosmetic composition.

Advantageous Effects

The cosmetic product having an excellent UV-blocking effect according to the present invention is manufactured by adding the optimum amount of the hollow pearlescent pigment to the cosmetic composition. Thus, the cosmetic product has an excellent UV-blocking effect, and whitening thereof can be minimized. In addition, the cosmetic product has a good feeling in use and good adhesion to the skin, and is not glossy and sticky after application to the skin.

Furthermore, according to the present invention, a portion of the plate-like flake matrix is removed by acid treatment, and then the remaining portion of the plate-like flake matrix is completely removed by alkali treatment. Thus, the hollow pearlescent pigment is light in weight due to its hollow structure, and may exhibit excellent masking and blocking functions due to its hollow structure. In addition, it may exhibit excellent UV-blocking effects and overcome the whitening problem.

Meanwhile, in the case of skin care cosmetics and color makeup cosmetics, including BB cream, foundation, makeup base, primer, skin cover, powder pack, two-way cake and loose powder cosmetics, pearlescent pigments are frequently used to make the cosmetic contents bright and elegant. However, the use of the pearlescent pigments has a problem in that the cosmetics are pearlescent and shiny on the face after application to the skin, and for this reason, consumers hesitate to use the cosmetics.

When the hollow pearlescent pigment is used in order to overcome this problem, the cosmetics can be pearlescent and shiny before application, so that they are distinguishable from general cosmetic products. After application, the cosmetics are not substantially pearlescent or shiny, and only fine white powder (titanium dioxide) remains uniformly on the skin to improve skin tone. In addition, since the cosmetics are not substantially pearlescent and shiny on the face after application, consumers may use the cosmetics without hesitation.

BEST MODE

Figure 1:
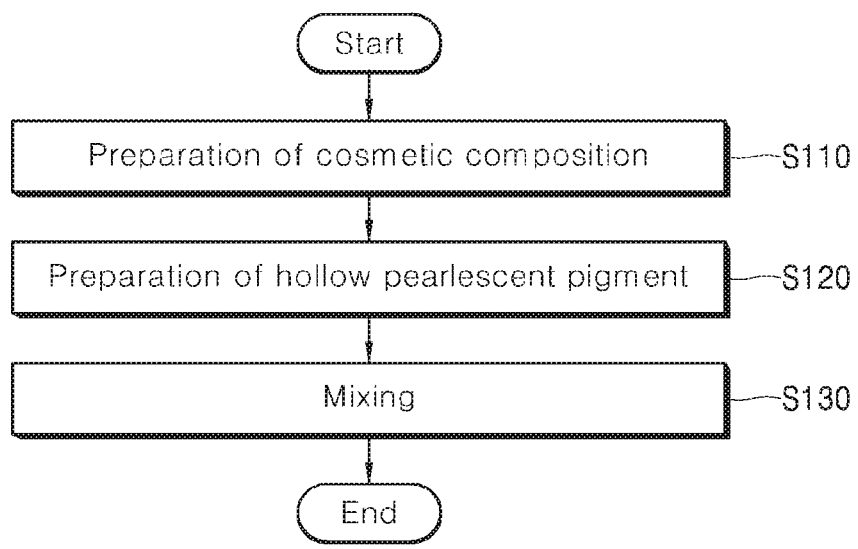
FIG. 1 is a flow chart showing a method for manufacturing a cosmetic product having an excellent UV-blocking effect according to an embodiment of the present invention.

The advantages and features of the present invention, and the way of attaining them, will become apparent with reference to the exemplary embodiments described below in conjunction with the accompanying drawings. However, the present invention is not limited to the exemplary embodiments disclosed below and can be embodied in a variety of different forms; rather, these embodiments are provided so that this disclosure will be thorough and complete, and will fully convey the scope of the present invention to those skilled in the art. The scope of the present invention will be defined by the appended claims. Like reference numerals refer to like elements throughout the specification and the accompanying figures.

Hereinafter, a cosmetic product having an excellent UV-blocking effect according to a preferred embodiment of the present invention and a manufacturing method thereof will be described in detail with reference to the accompanying drawings.

A cosmetic product having an excellent UV-blocking effect according to an embodiment of the present invention includes a cosmetic composition and a hollow pearlescent pigment.

As used herein, the term "cosmetic composition" refers to a raw material for manufacturing general cosmetics, including color makeup cosmetics and skin care cosmetics.

Herein, the color makeup cosmetics include base makeup products such as blemish balm (BB) cream, foundation, makeup base, primer, skin cover, powder pack, two-way cake, and loose powder; eye cosmetic products such as eye shadow, eye liner, mascara, and eye brow; cheek makeup products such as blusher, highlighter, and shading; and lip cosmetic products such as lipstick, lip gloss, lip tint, lip balm, lip lacquer, and liquid rouge.

The skin care cosmetics include sun protection cream, toner, emulsion, cream, essence, ampoule, cleansing foam, and hair cosmetic products such as shampoo and rinse.

The hollow pearlescent pigment that is added to the cosmetic composition serves to impart UV-blocking function to the cosmetic composition and suppress whitening of the cosmetic composition. Furthermore, the hollow pearlescent pigment that is added to the cosmetic composition serves to improve feeling and adhesion to the skin in use and enable the cosmetic composition to not be glossy and sticky after application to the skin.

To this end, the hollow pearlescent pigment is preferably added in an amount of 1 to 15 parts by weight, more preferably 5 to 10 parts by weight, based on 100 parts by weight of the cosmetic composition. If the amount of hollow pearlescent pigment added is less than 1 part by weight based on 100 parts by weight of the cosmetic composition, it may hardly exhibit the above-described effects, due to its very low content. On the other hand, if the amount of hollow pearlescent pigment added is more than 15 parts by weight based on 100 parts by weight of the cosmetic composition, the viscosity of an oil dispersion formulation or emulsion formulation containing the hollow pearlescent pigment added thereto may increase so that the feeling of the formulation in use will be reduced, and the formability of a compressed powder product containing the hollow pearlescent pigment added thereto may decrease. In addition, in this case, the production cost may increase, indicating that addition of the hollow pearlescent pigment in an amount of more than 15 parts by weight is disadvantageous in terms of economic efficiency.

The hollow pearlescent pigment has a hollow core and a metal oxide coating layer surrounding a portion or the whole of the hollow core. Herein, the metal oxide coating layer is preferably formed to a thickness of 0.1 to 3 µm. If the thickness of the metal oxide coating layer is out of the above-specified range, it may have poor light reflection efficiency.

For preparation of the hollow pearlescent pigment, a portion of the plate-like flake matrix is removed by acid treatment, and then the remaining portion of the plate-like flake matrix is completely removed by alkali treatment. Thus, the hollow pearlescent pigment is light in weight due to its hollow structure, and may exhibit excellent masking and blocking functions due to its hollow structure. In addition, it may exhibit excellent UV-blocking effects and overcome the whitening problem.

The cosmetic product having an excellent UV-blocking effect according to the embodiment of the present invention is manufactured by adding the optimum amount of the hollow pearlescent pigment to the cosmetic composition. Thus, the cosmetic product has an excellent UV-blocking effect, and whitening thereof can be minimized. In addition, the cosmetic product has a good feeling in use and good adhesion to the skin, and is not glossy and sticky after application to the skin.

Hereinafter, the method for manufacturing the cosmetic product having an excellent UV-blocking effect according to the embodiment of the present invention will be described in further detail with reference to the accompanying drawings.

FIG. 1 is a flow chart showing a method for manufacturing a cosmetic product having an excellent UV-blocking effect according to an embodiment of the present invention.

Referring to FIG. 1, the method for manufacturing the cosmetic product having an excellent UV-blocking effect according to the embodiment of the present invention includes the steps of: (S110) preparing a cosmetic composition; (S120) preparing a hollow pearlescent pigment; and (S130) mixing.

Preparation of Cosmetic Composition

Step (S110) of preparing a cosmetic composition, the cosmetic composition is prepared.

As used herein, the term "cosmetic composition" refers to a raw material for manufacturing general cosmetics, including color makeup cosmetics and skin care cosmetics.

Herein, the color makeup cosmetics include base makeup products such as blemish balm (BB) cream, foundation, makeup base, primer, skin cover, powder pack, two-way cake, and loose powder; eye cosmetic products such as eye shadow, eye liner, mascara, and eye brow; cheek makeup products such as blusher, highlighter, and shading; and lip cosmetic products such as lipstick, lip gloss, lip tint, lip balm, lip lacquer, and liquid rouge.

The skin care cosmetics include sun protection cream, toner, emulsion, cream, essence, ampoule, cleansing foam, and hair cosmetic products such as shampoo and rinse.

Preparation of Hollow Pearlescent Pigment

Step (S120) of preparing a hollow pearlescent pigment, the hollow pearlescent pigment is prepared. Step (S120) of preparing the hollow pearlescent pigment may include a coating process, an acid treatment process, a base treatment, and a drying process.

In the coating process, a metal oxide is coated on a plate-like flake matrix to form a metal oxide coating layer. Herein, the plate-like flake matrix may include one or more selected from among mica, plate-like silica, and glass flakes. Among them, mica is preferably used. Mica that is used in the present invention may be synthetic mica or natural mica. Preferably, synthetic mica is used. The plate-like flake matrix that is used in the present invention may be either a powder obtained by grinding and sieving or a powder obtained by grinding and sieving prepared powder.

The plate-like flake matrix that is used in the present invention preferably has an average particle diameter of 10 to 150 μm. Where the average particle diameter of the plate-like flake matrix is less than 10 μm, the plate-like flake matrix gradually becomes more spherical as the coating thickness increases during coating of the surface of the plate-like flake matrix, thereby reducing the aspect ratio of the plate-like flake matrix. When the aspect ratio is reduced, diffuse reflection will occur, resulting in light scattering. In addition, in this case, a uniform color having a uniform refractive index will not appear. On the other hand, if the average particle diameter of the plate-like flake matrix is more than 150 μm, the area of the surface to be coated will increase, making it possible to form a coating layer for exhibiting a particular color.

The metal oxide may include one or more selected from among $TiO_2$, $SiO_2$, $Al_2O_3$, $ZrO_2$ and $SnO_2$. The metal oxide preferably has an average particle diameter of 10 nm to 100 nm. If the average particle diameter of the metal oxide is less than 10 nm, it may be difficult to coat the metal oxide on the plate-like flake matrix. On the other hand, if the average particle diameter of the metal oxide is more than 100 nm, it may be difficult to achieve a desired light reflection effect, due to light scattering.

The metal oxide coating layer is preferably formed to a thickness of 0.1 to 3 μm. If the thickness of the metal oxide coating layer is less than 0.1 μm, the effect of reflecting infrared rays may be insignificant. On the other hand, if the thickness of the metal oxide coating layer is more than 3 μm, it may merely increase the production cost without further increasing the effect, resulting in disadvantages in terms of economic efficiency.

In the acid treatment process, the plate-like flake matrix having the metal oxide coating layer formed thereon is suspended in deionized water, and in this state, it is subjected to acid treatment using an acidic solution, followed by refluxing, washing and filtration.

In the acid treatment, ultrasonic waves are preferably applied to the suspension at a frequency of 15 to 40 kHz and a power of 70 to 110 W while the suspension is agitated at a speed of 300 to 500 rpm. Where ultrasonic waves are applied during the acid treatment, the suspension may have extreme conditions, including a temperature of 5000K, a pressure of about 1000 bar, and a heating/cooling rate of $10^{10}$ K/s, when bubbles collapse after a certain amount of time. This may maximize the efficiency of diffusion.

If the agitation speed is less than 300 rpm or the power of ultrasonic waves is less than 70 W, agitation can be insufficient. On the other hand, if the agitation speed is more than 500 rpm or the power of ultrasonic waves is more than 110 W, the particles can be severely broken to generate a large amount of unnecessary small particles, making it difficult to control the particle size to a desired size or to carry out subsequent processes.

The acidic solution that is used in the present invention may be a solution of one or more selected from sulfuric acid, phosphoric acid and nitric acid. The acidic solution preferably has a concentration of 40 to 60 wt %. If the concentration of the acidic solution is less than 40 wt %, dissolution of the plate-like flake matrix during the acid treatment may not be easily achieved, making it difficult to obtain a hollow structure. On the other hand, the concentration of the acidic solution is more than 60 wt %, a problem may arise in that the metal oxide coating layer is also dissolved together with the plate-like flake matrix due to the excessively high concentration.

In this step, the refluxing is preferably performed at a temperature of 80 to 120° C. for 4 to 6 hours. If the refluxing temperature is lower than 80° C. or the refluxing time is less than 4 hours, sufficient dissolution cannot be ensured, and non-uniform hollow spheres may be produced so that surface cracks can be caused by undissolved flakes. On the other hand, if the refluxing temperature is higher than 120° C. or the refluxing time is more than 6 hours, the coating layer of the hollow sphere can be broken by agitation or the metal oxide coating layer can be separated.

In the base treatment process, the material resulting from the acid treatment process is suspended in deionized water, and in this state, it is subjected to alkali treatment using a basic solution, followed by refluxing and filtration.

The basic solution that is used in the present invention is preferably a strongly basic solution having a concentration of 40-55 wt %. Specifically, the basic solution may be a solution of one or more selected from among sodium hydroxide and potassium hydroxide.

If the concentration of the basic concentration is lower than 40 wt %, the plate-like flake matrix having the metal oxide coating layer formed thereon, which has been subjected to the acid treatment, may not be completely dissolved so that a hollow structure cannot be formed. On the other hand, if the concentration of the basic solution is higher than 55 wt %, a problem may arise in that the metal oxide coating layer is also dissolved together with the plate-like flake matrix due to the excessively high concentration.

In the base treatment process, the refluxing is preferably performed at a temperature of 50 to 70° C. for 1 to 3 hours.

In the present invention, the plate-like flake matrix having the metal oxide coating layer formed thereon is subjected to acid treatment with sulfuric acid to thereby remove at least half of the plate-like flake matrix, and in this state, the plate-like flake matrix is subjected to alkali treatment. Thus, the plate-like flake matrix can be completely removed, thereby providing a pearlescent pigment having a hollow structure.

In the drying process, the material resulting from the base treatment process is dried, thereby obtaining a metal oxide coating layer having a hollow structure, from which the plate-like flake matrix was removed.

Herein, the drying is preferably performed at a temperature of 100 to 150° C. for 10 to 120 minutes. If the drying temperature is lower than 100° C., the drying time may increase, resulting in reductions in economic efficiency and productivity. On the other hand, if the drying temperature is higher than 150° C., aggregation between the particles may undesirably increase.

The hollow pearlescent pigment prepared as described above has a hollow core and a metal oxide coating layer surrounding to a portion or the whole of the hollow core. Herein, the metal oxide coating layer is preferably formed to a thickness of 0.1 to 3 μm. If the thickness of the metal oxide coating layer is out of the above-specified range, the pigment may have poor light reflection efficiency.

According to the present invention, a portion of the plate-like flake matrix is removed by acid treatment, and then the remaining portion of the plate-like flake matrix is completely removed by alkali treatment. Thus, the hollow pearlescent pigment is light in weight due to its hollow structure, and may exhibit excellent masking and blocking functions due to its hollow structure. In addition, it may exhibit excellent UV-blocking effects and overcome the whitening problem.

Mixing

In step (S130) of mixing, the hollow pearlescent pigment is mixed with the cosmetic composition.

In this mixing step, the hollow pearlescent pigment is preferably added to the cosmetic composition in an amount of 1 to 15 parts by weight, more preferably 5 to 10 parts by weight, based on 100 parts by weight of the cosmetic composition. If the amount of hollow pearlescent pigment added is less than 1 part by weight based on 100 parts by weight of the cosmetic composition, it may hardly exhibit the above-described effects, due to its very low content. On the other hand, if the amount of hollow pearlescent pigment added is more than 15 parts by weight based on 100 parts by weight of the cosmetic composition, the viscosity of an oil dispersion formulation or emulsion formulation containing the hollow pearlescent pigment added thereto may increase so that the feeling of the formulation in use will be reduced, and the formability of a compressed powder product containing the hollow pearlescent pigment added thereto may decrease. In addition, in this case, the production cost may increase, indicating that addition of the hollow pearlescent pigment in an amount of more than 15 parts by weight is disadvantageous in terms of economic efficiency.

The cosmetic product having an excellent UV-blocking effect according to the embodiment of the present invention, which is manufactured through the above-described steps (S110 to S130), contains the optimum amount of the hollow pearlescent pigment added to the cosmetic composition. Thus, the cosmetic product has an excellent UV-blocking effect, and whitening thereof can be minimized. In addition, the cosmetic product has a good feeling in use and good adhesion to the skin, and is not glossy and sticky.

Furthermore, for manufacturing of the cosmetic product having an excellent UV-blocking effect according to the present invention, the plate-like flake matrix used to prepare the hollow pearlescent pigment that is added to the cosmetic composition is partially removed by acid treatment, and then the remaining portion of the plate-like flake matrix is completely removed by alkali treatment. Thus, the hollow pearlescent pigment is light in weight due to its hollow structure, and may exhibit excellent masking and blocking functions due its hollow structure. In addition, it may exhibit excellent UV-blocking effects and overcome the whitening problem.

In the case of skin care cosmetics and color makeup cosmetics, including BB cream, foundation, makeup base, primer, skin cover, powder pack, two-way cake and loose powder cosmetics, pearlescent pigments are frequently used to make the cosmetic contents bright and elegant. However, the use of the pearlescent pigments has a problem in that the cosmetics are pearlescent and shiny on the face after application to the skin, and for this reason, consumers hesitate to use the cosmetics.

When the hollow pearlescent pigment is used in order to overcome this problem, the cosmetics can be pearlescent and shiny before application, so that they are distinguishable from general cosmetic products. After application, the cosmetics are not substantially pearlescent or shiny, and only fine white powder (titanium dioxide) remains uniformly on the skin to improve skin tone. In addition, since the cosmetics are not substantially pearlescent and shiny on the face, consumers may use the cosmetics without hesitation.

EXAMPLES

Hereinafter, the present invention will be described in further detail with reference to preferred examples. It is to be understood, however, that these examples are for illustrative purposes and are not intended to limit the scope of the present invention in any way.

The contents not described herein can be readily envisioned by those skilled in the art, and thus the detailed description thereof is omitted.

1. Measurement of UV-Blocking Effects

In order to compare the UV-blocking effect of a hollow pearlescent pigment with those of two types of titanium dioxide, which have generally been used in cosmetics for UV blocking purposes, oil-based sun protection creams of Example 1 and Comparative Examples 1 and 2 were prepared using the compositions shown in Table 1 below. The content of titanium dioxide was set at 25 wt % which is the maximum value acceptable for cosmetics, and the content of the hollow pearlescent pigment was also set at 25 wt %.

TABLE 1

(unit: wt %)

| Phase | Component | Example 1 | Comparative Example 1 | Comparative Example |
|---|---|---|---|---|
| A | Caprylic/capric triglyceride | Balance | Balance | Balance |
|  | Beeswax | 1.00 | 1.00 | 1.00 |
|  | Cyclopentasiloxane | 15.00 | 15.00 | 15.00 |
|  | Dimethicone | 20.00 | 20.00 | 20.00 |
|  | Preservative | 0.30 | 0.30 | 0.30 |
| B | Polymethylmethacrylate | 1.00 | 1.00 | 1.00 |
|  | Titanium dioxide (TiO$_2$ CR50) | — | 25.0 | — |
|  | Titanium dioxide (TiO$_2$ 060 AS) | — | — | 25.0 |
|  | Hollow pearlescent pigment | 25.0 | — | — |

1) Preparation Method

The components of phase A were uniformly mixed using an agitator at 80° C.

The components of phase B were uniformly mixed using a mixer, and then added to phase A, followed by uniform dispersion.

Next, the resulting mixtures were cooled to 30° C., thereby obtaining oil-based sun protection creams of Example 1 and Comparative Examples 1 and 2.

The hollow pearlescent pigment in phase B was prepared in the following manner.

First, 200 mL of deionized water and 100 g of TiO$_2$-coated mica were placed in a 3-L Morton flask and suspended. Then, the reactor was equipped with a condenser, and 400 mL of H$_2$SO$_4$ was added to the reactor, and in this state, the content of the reactor was agitated at 400 rpm while applying ultrasonic waves at a frequency of 30 kHz and a power of 90 W.

Next, the solution was refluxed at 100° C. for 6 hours and cooled, and then 800 mL of water was added thereto, followed by refluxing. Then, the solution was filtered through filter paper, and the filtrate was washed four times with 1000 mL of water, thereby obtaining acid-treated powder.

The acid-treated powder was placed in a 3-L flask, and 800 mL of deionized water was added thereto. The suspension was agitated at a speed of 400 rpm, and 400 mL of an aqueous solution containing 50 wt % of NaOH was added thereto. Then, the solution was refluxed at 60° C. for 4 hours.

Next, the solution was filtered through filter paper, and the filtrate was washed four times with 800 mL of water and dried at 120° C., thereby obtaining a hollow pearlescent pigment.

Table 2 below shows the results of measurement of properties of the oil-based sun protection creams prepared in Example 1 and Comparative Examples 1 and 2. Furthermore, FIGS. 2 to 4 show the results of measuring the UV-blocking abilities of the oil-based sun protection creams prepared in Example 1 and Comparative Examples 1 and 2.

TABLE 2

|  | Example 1 |  | Comparative Example 1 |  | Comparative Example 2 |  |
|---|---|---|---|---|---|---|
|  | Value | S.D. | Value | S.D. | Value | S.D. |
| SPF | 56.32 | 36.18 | 25.34 | 4.84 | 4.1 | 1.12 |
| UVA/UVB ratio | 0.726 | 0.01 | 1.008 | 0.01 | 0.985 | 0.01 |
| Boots Star Rating (2004) | 3 | Good | 5 | Ultra | 5 | Ultra |
| UVA I/UV ratio | 0.83 | High | 1 | High | 1 | High |
| Max % T COV | 61.1 | — | 18.23 | — | 23.93 | — |
| Critical wavelength | 387.2 | 0 | 389.1 | 0.11 | 389.3 | 0.16 |
| Curve area | 161.95 | 20.85 | 154.74 | 7.27 | 66.48 | 10.98 |
| UVA PF | 27.9 | 10.91 | 25.71 | 3.81 | 4.07 | 0.96 |
| Erythema UVA PF | 34.34 | 13.01 | 26.13 | 4.21 | 4.12 | 1 |

Figure 2:
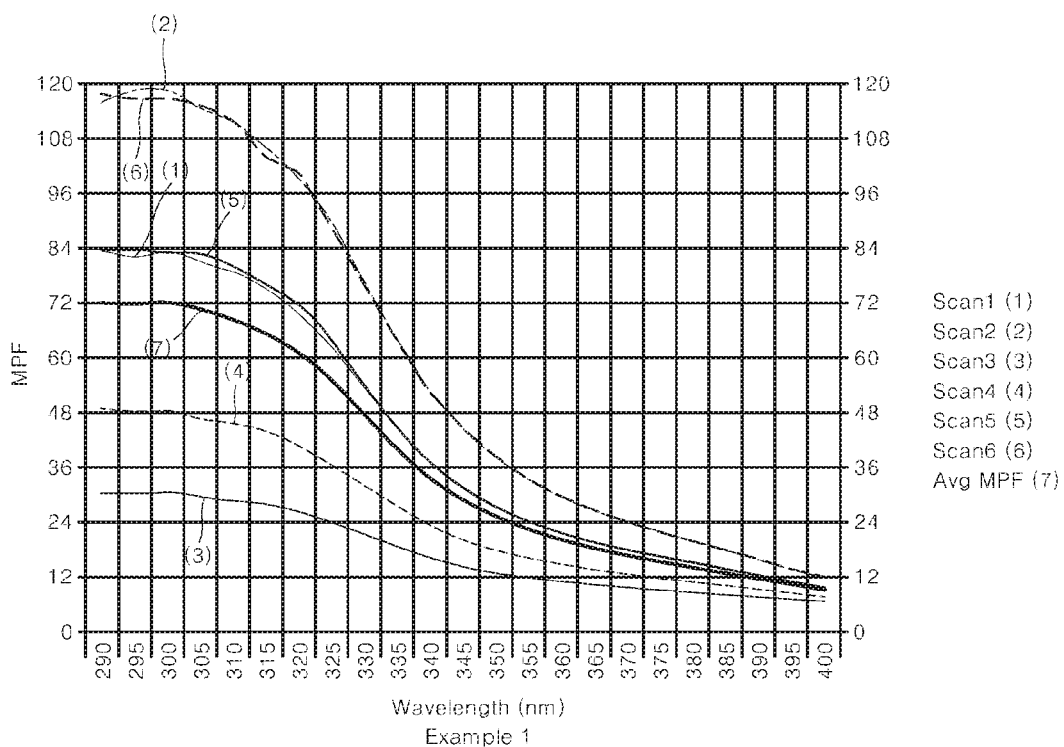
FIG. 2 is a graph showing the results of measuring the UV-blocking ability of Example 1.
Figure 3:
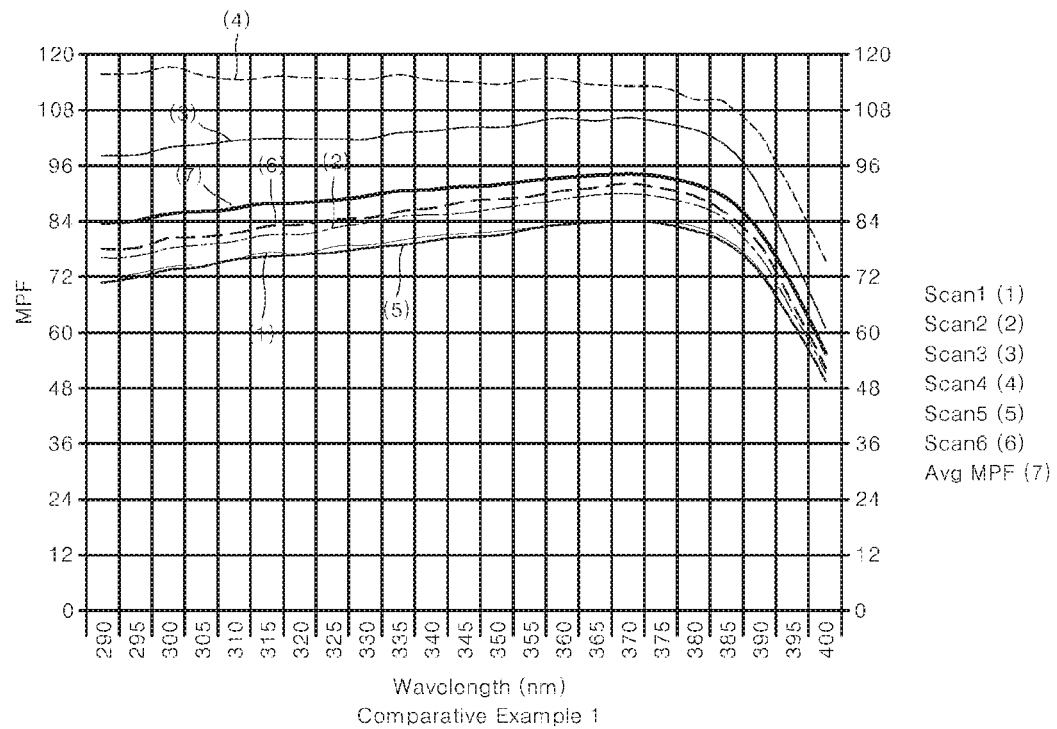
FIG. 3 is a graph showing the results of measuring the UV-blocking ability of Comparative Example 1.
Figure 4:
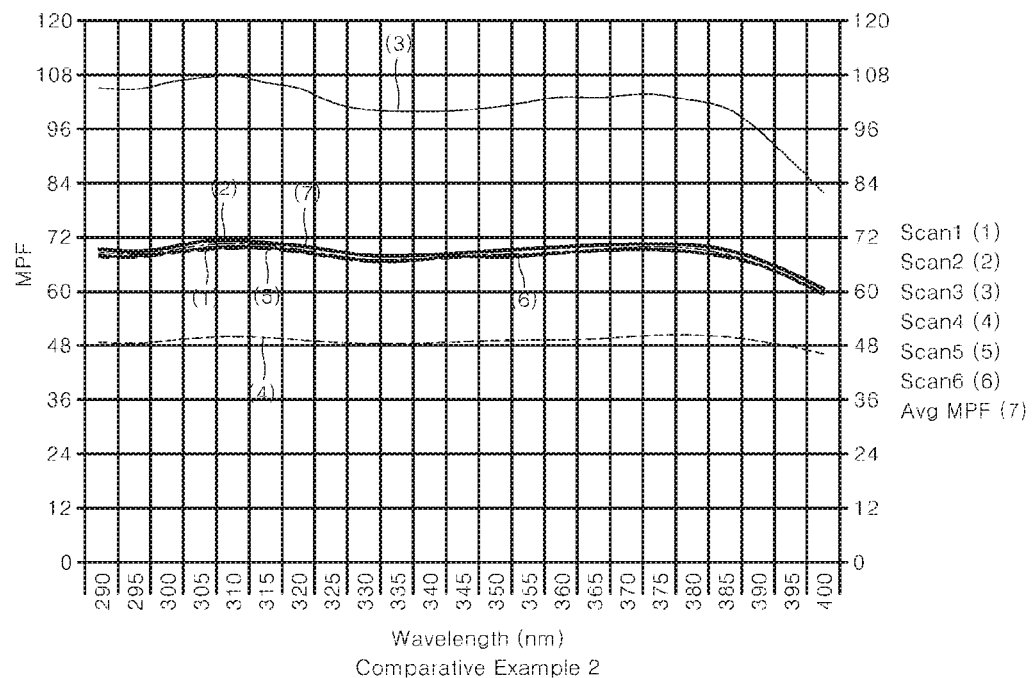
FIG. 4 is a graph showing the results of measuring the UV-blocking ability of Comparative Example 2.

As can be seen in Tables 1 and 2 and FIGS. 2 to 4, Example 1 showed an average SPF value of 56.32 and an average UVA PF value of 27.9.

Unlike this, Comparative Example 1 showed an average SPF value of 25.34 and an average UVA PF value of 25.71, and Comparative Example 2 showed an average SPF value of 4.1 and an average UVA PF value of 4.07.

As can be seen from the above-described experimental results, the sun protection factor (SPF) of Example 1 was significantly higher than that of titanium dioxide that has been frequently used for UV blocking purposes.

2. Example of Application of Sun Protection Cream

Sun protection creams of Example 2 and Comparative Examples 3 and 4 were prepared using the compositions shown in Table 3 below.

TABLE 3

(unit: wt %)

| Phase | Component | Example 2 | Comparative Example 3 | Comparative Example 4 |
|---|---|---|---|---|
| A | Purified water | Balance | Balance | Balance |
|  | Glycerin | 4.00 | 4.00 | 4.00 |
|  | Butylene glycol | 8.00 | 8.00 | 8.00 |
| B | Beeswax | 1.00 | 1.00 | 1.00 |
|  | Cyclopentasiloxane | 15.00 | 15.00 | 15.00 |
|  | PEG-10 dimethicone | 4.00 | 4.00 | 4.00 |
|  | Methylhexyl methoxycinnamate | 7.00 | 7.00 | 7.00 |
|  | Isododecane/disteardimonium hectorite/propylene carbonate | 2.00 | 2.00 | 2.00 |
|  | Dimethicone | 7.00 | 7.00 | 7.00 |
|  | Preservative | 0.30 | 0.30 | 0.30 |
| C | Polymethylmethacrylate | 1.00 | 1.00 | 1.00 |
|  | Titanium dioxide (TiO$_2$ CR50) | — | 10.0 | — |
|  | Titanium dioxide (TiO$_2$ 060 AS) | — | — | 10.0 |
| D | Hollow pearlescent pigment | 10.0 | — | — |

1) Preparation Method

The components of phase B were uniformly mixed at 80° C.

The components of phase C were mixed uniformly, and then added to phase B and dispersed uniformly.

Next, the mixture of phase B and phase C was emulsified using a homogenizer while phase A mixed at 80° C. was slowly added thereto.

Next, the emulsion in Example 2 was cooled to 40° C., and then phase D was added thereto, followed by emulsification for 5 minutes and cooling to 30° C., and the emulsions in Comparative Examples 3 and 4 were cooled to 30° C., thereby obtaining sun protection creams.

Herein, phase D was prepared in the following manner.

First, 200 mL of deionized water and 100 g of TiO$_2$-coated mica were placed in a 3-L Morton flask and suspended. Then, the reactor was equipped with a condenser, and 400 mL of H$_2$SO$_4$ was added to the reactor, and in this state, the content of the reactor was agitated at 400 rpm while applying ultrasonic waves at a frequency of 30 kHz and a power of 90 W.

Next, the solution was refluxed at 100° C. for 6 hours and cooled, and then 800 mL of water was added thereto, followed by refluxing. Then, the solution was filtered through filter paper, and the filtrate was washed four times with 1000 mL of water, thereby obtaining acid-treated powder.

The acid-treated powder was placed in a 3-L flask, and 800 mL of deionized water was added thereto. The suspension was agitated at a speed of 400 rpm, and 400 mL of an aqueous solution containing 50 wt % of NaOH was added thereto. Then, the solution was refluxed at 60° C. for 4 hours.

Next, the solution was filtered through filter paper, and the filtrate was washed four times with 800 mL of water and dried at 120° C., thereby obtaining a hollow pearlescent pigment.

As described in Example 2, the hollow pearlescent pigment is used as a raw material for preparing sun protection cream for blocking UV rays. In this case, as described with reference to Tables 1 and 2 and FIGS. 2 to 4, it can be anticipated that the sun protection cream will have an excellent UV-blocking effect. In Comparative Examples 3 and 4, conventional titanium dioxide is used as a UV blocker. In this case, whitening of the sun protection cream is severe, and the feeling of the sun protection cream in use is hard and poor, because the particle size of the titanium dioxide is very small. However, the hollow pearlescent pigment used in Example 2 can overcome the whitening-associated problem that is the shortcoming of titanium dioxide, and it also improves the feeling of the sun protection cream due to its large particle size.

Accordingly, the hollow pearlescent pigment used in Example 2 provides an excellent UV-blocking effect and improves quality in various terms.

2) Evaluation of Properties

In order to examine the effects of using the sun protection creams of Example 2 and Comparative Examples 3 and 4, forty women (20 to 40 years old) were allowed to use the sun protection creams for 15 days, and the resulting scores were averaged for evaluation.

Evaluation items were whitening, adhesion, non-sticky property, non-glossy property, and feeling in use, and the results are shown in Table 4 below.

TABLE 4

|  | Whitening | Adhesion | Non-sticky property | Non-glossy property | Feeling in use |
|---|---|---|---|---|---|
| Example 2 | 3.2 | 4.6 | 4.5 | 3.9 | 4.5 |
| Comparative Example 3 | 4.2 | 3.3 | 3.0 | 2.6 | 2.9 |
| Comparative Example 4 | 4.5 | 3.4 | 3.2 | 2.5 | 2.5 |

\* Higher values indicate higher scores, except for whitening.
\* Criteria for evaluation (adhesion, non-sticky property, non-sticky property, and feeling in use)
1: very poor, 2: poor, 3: moderate, 4: good, and 5: very good.
\* Criteria for evaluation (whitening)
1: very less, 2: less, 3: moderate, 4: more, and 5: very more.

As can be seen in Tables 3 and 4 above, Example 2 showed less whitening than Comparative Examples 3 and 4. Considering such results together with the results of the UV-blocking effect as described above, it can be seen that the sun protection cream of Example 2 has an excellent UV-blocking effect and, at the same time, can overcome the whitening problem of conventional sun protection cream.

In addition, it could be seen that the sun protection cream of Example 2 was improved in terms of quality properties, including adhesion, non-sticky property, non-glossy property, and feeling in use. This is believed to be because the sun protection cream of Example has good adhesion due to uniform application to the skin, and a good feeling in use due to its lightweight, and has high oil absorption that reduces stickiness or glossiness.

3. Example of Application of BB Cream

BB creams of Example 3 and Comparative Example 5 were prepared using the compositions in Table 5 below.

TABLE 5

(unit: wt %)

| Phase | Component | Example 3 | Comparative Example 5 |
|---|---|---|---|
| A | Purified water | Balance | Balance |
|  | Glycerin | 4.00 | 4.00 |
|  | Butylene glycol | 4.00 | 4.00 |
| B | Beeswax | 1.50 | 1.50 |
|  | Dimethicone | 18.00 | 18.00 |
|  | PEG-10 dimethicone | 4.00 | 4.00 |
|  | Caprylic/capric triglyceride | 7.00 | 7.00 |
|  | Isododecane/disteardimonium hectorite/propylene carbonate | 2.00 | 2.00 |
|  | Phenyl trimethicone | 7.00 | 7.00 |
|  | Preservative | 0.30 | 0.30 |
| C | Iron oxide (surface-treated with methicone) | 1.00 | 1.00 |

TABLE 5-continued (unit: wt %)

| Phase | Component | Example 3 | Comparative Example 5 |
|---|---|---|---|
|  | Polymethylmethacrylate | 1.00 | 1.00 |
|  | Titanium dioxide (surface-treated with methicone) | 4.00 | 4.00 |
| D | Hollow pearlescent pigment | 5.00 | — |

1) Preparation Method

The components of phase B were uniformly mixed at 80° C.

The components of phase C were mixed uniformly, and then added to phase B and dispersed uniformly.

Next, the mixture of phase B and phase C was emulsified using a homogenizer while phase A mixed at 80° C. was slowly added thereto.

Next, the emulsion in Example 3 was cooled to 40° C., and then phase D was added thereto, followed by emulsification for 5 minutes and cooling to 30° C., and the emulsion in Comparative Example 5 was cooled to 30° C., thereby obtaining BB creams.

Herein, as phase D, the same hollow pearlescent pigment as used in Example 2 was used.

2) Evaluation of Properties

In order to examine the effects of using the BB creams of Example 3 and Comparative Example 5, forty women (20 to 40 years old) were allowed to use the BB creams for 15 days, and the resulting scores were averaged for evaluation.

Evaluation items were covering ability, adhesion, non-sticky property, non-glossy property, and feeling in use, and the results are shown in Table 6 below.

TABLE 6

|  | Covering ability | Adhesion | Non-sticky property | Non-glossy property | Feeling in use |
|---|---|---|---|---|---|
| Example 3 | 4.2 | 4.8 | 4.4 | 4.3 | 4.5 |
| Comparative Example 5 | 3.2 | 3.3 | 3.1 | 2.9 | 3.4 |

\* Higher values indicate higher scores.
\* Criteria for evaluation
1: very poor, 2: poor, 3: moderate, 4: good, and 5: very good.

As can be seen in Table 6 above, the BB cream of Example 3, containing the hollow pearlescent pigment, is applied uniformly to the skin with high covering ability and adhesion. Furthermore, it is considered that, since the BB cream of Example 3 has a good feeling in use due to its lightweight and has high oil absorption that reduces stickiness and glossiness, thereby expressing a natural skin.

4. Example of Application of Pressed Eye Shadow

Pressed eye shadows of Example 4 and Comparative Example 6 were prepared using the compositions shown in Table 7 below.

TABLE 7

(unit: wt %)

| Phase | Component | Example 4 | Comparative Example 6 |
|---|---|---|---|
| A | Talc | Balance | Balance |
|  | Mica | 10.00 | 10.00 |
|  | Magnesium stearate | 3.00 | 3.00 |

TABLE 7-continued (unit: wt %)

| Phase | Component | Example 4 | Comparative Example 6 |
|---|---|---|---|
|  | Polymethylene | 3.00 | 3.00 |
|  | Polymethylmethacrylate | 3.00 | 3.00 |
| B | Colorant | 3.00 | 3.00 |
| C | Pearl pigment | 30.00 | 30.00 |
|  | Hollow pearlescent pigment | 5.00 | — |
| D | Diisostearyl malate | 4.00 | 4.00 |
|  | Isotridecyl isononanoate | 3.00 | 3.00 |
|  | Dimethicone | 3.00 | 3.00 |
|  | Preservative | 0.30 | 0.30 |

1) Preparation Method

Phase A and phase B were weighed, and then mixed uniformly using a mixer for 1 minute.

Next, phase C was added to the mixture of phase A and phase B and mixed uniformly using a mixer for 30 seconds.

Thereafter, phase D was added to the uniform mixture of phases A, B and C, and then mixed uniformly for 1 minute.

Next, a suitable amount of the resulting mixture was placed in a mold and molded using a press-molding machine, thereby obtaining pressed eye shadow.

As the hollow pearlescent pigment in phase C, the same hollow pearlescent pigment as used in Example 2 was used.

2) Evaluation of Properties

In order to examine the effects of using the pressed eye shadows of Example 4 and Comparative Example 6, forty women (20 to 40 years old) were allowed to use the pressed eye shadows, and the resulting scores were averaged for evaluation.

Evaluation items were feeling in use, adhesion, spreadability, and long-lasting ability, and the results are shown in Table 8 below.

TABLE 8

|  | Feeling in use | Adhesion | Spreadability | Long-lasting ability |
|---|---|---|---|---|
| Example 4 | 4.1 | 4.1 | 3.6 | 3.3 |
| Comparative Example 6 | 3.2 | 2.5 | 2.5 | 2.3 |

* Higher values indicate higher scores.
* Criteria for evaluation
1: very poor, 2: poor, 3: moderate, 4: good, and 5: very good.

As can be seen in Table 8, Example 4 was improved in terms of feeling, adhesion, spreadability and long-lasting ability compared to Comparative Example 6. This is believed to be because Example 4 is light in weight to exhibit an improved feeling or improved spreadability, and is applied uniformly to the skin with high adhesion to exhibit an improved long-lasting property.

5. Example of Application of Lip Gloss

Lip glosses of Example 5 and Comparative Example 7 were prepared using the compositions shown in Table 9 below.

TABLE 9

(unit: wt %)

| Phase | Component | Example 5 | Comparative Example 7 |
|---|---|---|---|
| A | Octyldodecanol | Balance | Balance |
|  | Polybutene | 65.00 | 65.00 |
|  | Diisostearyl malate | 8.00 | 8.00 |
|  | Sorbitan olivate | 3.00 | 3.00 |
|  | Preservative | 0.30 | 0.30 |
| B | Colorant | 3.00 | 3.00 |
| C | Pearl pigment | 5.00 | 5.00 |
|  | Hollow pearlescent pigment | 5.00 | — |

1) Preparation Method

The components of phase A were weighed and mixed uniformly using an agitator at 85° C.

Then, phase B was added to phase A and mixed uniformly until the colorant would be completely dispersed.

Next, phase C was added to the mixture of phase A and phase C and mixed uniformly, followed by cooling to 30° C., thereby obtaining lip gloss.

As the hollow pearlescent pigment of phase C, the same hollow pearlescent pigment as used in Example 2 was used.

2) Evaluation of Properties

In order to examine the effects of using the lip glosses of Example 5 and Comparative Example 7, forty women (20 to 40 years old) were allowed to use the lip glosses, and the resulting scores were averaged for evaluation.

Evaluation items were adhesion, non-sticky property, spreadability, and feeling in use, and the results are shown in Table 10 below.

TABLE 10

|  | Adhesion | Non-sticky property | Spreadability | Feeling in use |
|---|---|---|---|---|
| Example 5 | 4.0 | 3.5 | 3.8 | 3.5 |
| Comparative Example 7 | 3.8 | 2.3 | 3.1 | 2.9 |

* Higher values indicate higher scores.
* Criteria for evaluation
1: very poor, 2: poor, 3: moderate, 4: good, and 5: very good.

As can be seen in Table 10 above, the properties of Example 5 were improved compared to those of Comparative Example 7. Particularly, the non-sticky property of Example 5 was significantly improved. This is believed to be because the oil-based formulation of Example 5, having a high oil content, had high oil absorption.

6. Example of Application of Emulsion

Emulsions (skin care cosmetics) of Example 6 and Comparative Example 8 were prepared using the compositions shown in Table 11 below.

TABLE 11

(unit: wt %)

| Phase | Component | Example 6 | Comparative Example 8 |
|---|---|---|---|
| A | Purified water | Balance | Balance |
|  | Carbomer | 0.40 | 0.40 |
| B | Glycerin | 10.00 | 10.00 |
|  | Butylene glycol | 5.00 | 5.00 |
|  | Sodium chloride | 0.50 | 0.50 |
| C | Cetyl alcohol | 1.00 | 1.00 |
|  | Beeswax | 1.00 | 1.00 |
|  | Caprylic/capric triglyceride | 7.00 | 7.00 |

TABLE 11-continued (unit: wt %)

| Phase | Component | Example 6 | Comparative Example 8 |
|---|---|---|---|
| | Dimethicone | 2.00 | 2.00 |
| | Sorbitan sesquioleate | 0.80 | 0.80 |
| | Polysorbate 80 | 2.00 | 2.00 |
| | Preservative | 0.50 | 0.50 |
| D | Hollow pearlescent pigment | 5.00 | — |

1) Preparation Method

The components of phase A were weighed and mixed uniformly at 70° C.

Then, phase B was added to the uniform mixture of phase B and mixed uniformly for 5 minutes.

Then, the uniform mixture of phase A and phase B was emulsified using a homogenizer at 70° C. for 10 minutes while phase C was slowly added thereto.

Next, the emulsion in Example 6 was cooled to 40° C., and then phase D was added thereto, followed by emulsification for 5 minutes and cooling to 30° C., and the emulsion in Comparative Examples 8 was cooled to 30° C., thereby obtaining emulsions.

As phase D, the same hollow pearlescent pigment as used in Example 2 was used.

2) Evaluation of Properties

In order to examine the effects of using the emulsions of Example 6 and Comparative Example 8, forty women (20 to 40 years old) were allowed to use the emulsions, and the resulting scores were averaged for evaluation.

Evaluation items were covering ability, adhesion, non-sticky property, and feeling in use, and the results are shown in Table 12 below.

TABLE 12

| | Covering ability | Adhesion | Non-sticky property | Non-glossy property | Feeling in use |
|---|---|---|---|---|---|
| Example 6 | 3.1 | 4.9 | 4.8 | 4.8 | 4.0 |
| Comparative Example 8 | 1.0 | 3.2 | 2.9 | 3.1 | 3.3 |

* Higher values indicate higher scores.
* Criteria for evaluation
1: very poor, 2: poor, 3: moderate, 4: good, and 5: very good.

As can be seen in Table 12 above, the emulsion of Example 6 is applied thinly to the skin to make the skin tone white and has good adhesion to the skin. Furthermore, the emulsion of Example 6 has a good feeling due to its lightweight, and has high oil absorption that reduces stickiness or glossiness, thereby expressing the skin naturally.

As described above, in the case of skin care cosmetics, pearlescent pigments are frequently used to make the cosmetic contents bright and elegant. However, the use of the pearlescent pigments has a problem in that the cosmetics are pearlescent and shiny on the face after application to the skin, and for this reason, consumers hesitate to use the cosmetics.

When the hollow pearlescent pigment is used in order to overcome this problem, the cosmetics can be pearlescent and shiny before application, so that they are distinguishable from general cosmetic products. After application, the cosmetics are not substantially pearlescent or shiny, and only fine white powder (titanium dioxide) remains uniformly on the skin to improve skin tone. In addition, since the cosmetics are not substantially pearlescent and shiny on the face after application, consumers may use the cosmetics without hesitation.

Although the preferred embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A cosmetic product having an excellent UV-blocking effect, the cosmetic product comprising:
   a cosmetic composition; and
   a hollow pearlescent pigment having a hollow core, wherein
   the hollow pearlescent pigment consists of a metal oxide coating layer surrounding a portion or the whole of the hollow core, wherein the metal oxide coating layer is a layer consisting of $SiO_2$, a layer consisting of $Al_2O_3$, or a layer consisting of $SiO_2$ and $Al_2O_3$,
   an amount of the hollow pearlescent pigment ranges from 1 part by weight to 15 parts by weight based on 100 parts by weight of the cosmetic composition,
   a shape of the hollow core corresponds to a shape of a mica flake, and
   an average diameter of the hollow core ranges from 10 μm to 150 μm.

2. The cosmetic product of claim 1, wherein the hollow pearlescent pigment is added in an amount of 5 to 10 parts by weight based on 100 parts by weight of the cosmetic composition.

3. The cosmetic product of claim 1, wherein the metal oxide coating layer has a thickness of 0.1 to 3 μm.

4. The cosmetic product of claim 1, wherein the hollow pearlescent pigment is manufactured by coating the mica flake with a metal oxide, and removing the mica flake to form the hollow core.

* * * * *